(12) United States Patent
Lam et al.

(10) Patent No.: US 7,939,712 B2
(45) Date of Patent: May 10, 2011

(54) METHOD TO ALLEVIATE ABIOTIC STRESS IN PLANTS BY EXPRESSION OF MITOCHONDRIAL-TARGETED PURPLE ACID PHOSPHATASE

(75) Inventors: Hon-Ming Lam, Shatin (CN); Samuel Sai Ming Sun, Shatin (CN); Gui Hua Shao, Beijing (CN)

(73) Assignee: The Chinese University of Hong Kong, Hong Kong (CN)

( * ) Notice: Subject to any disclaimer, the term of this patent is extended or adjusted under 35 U.S.C. 154(b) by 908 days.

(21) Appl. No.: 11/893,832

(22) Filed: Aug. 17, 2007

(65) Prior Publication Data
US 2009/0038029 A1    Feb. 5, 2009

Related U.S. Application Data

(60) Provisional application No. 60/838,769, filed on Aug. 18, 2006.

(51) Int. Cl.
*C12N 15/05* (2006.01)
*C12N 15/29* (2006.01)
*C12N 15/82* (2006.01)

(52) U.S. Cl. ........................ 800/278; 435/468

(58) Field of Classification Search ........................ None
See application file for complete search history.

(56) References Cited

U.S. PATENT DOCUMENTS

2002/0160378 A1   10/2002   Harper et al.
2004/0009476 A9    1/2004   Harper et al.

OTHER PUBLICATIONS

Liao et al. GmPAP3, a novel purple acid phosphatase-like gene in soybean induced by NaCl stress but not phosphorus deficiency. (2003) Gene; vol. 318; pp. 103-111.*
Li et al., New Phytologist (2008) 178:80-91.
Allan et al., Plant Cell (1997) 9:1559-1572.
An, Plant Physiol. (1985) 79:568-570.
Bechtold and Pelletier, Martinez-Zapater and Salinas, eds., *Arabidopsis Protocols*, Humana Press Inc., Totowa, 1993, pp. 259-266.
Brears et al., Plant Physiol. (1993) 103:1285-1290.
Delong et al., Food. Chem. (2002) 50:248-254.
Douce et al., Methods Enzymol. (1987) 148:403-415.
Jiang and Rogers, J. Cell Biol. (1998) 143:1183-1199.
Liao et al., Gene (2003) 318:103-111.
Maxwell et al., PNAS USA (1999) 96:8271-8276.
Sattler et al., Plant Cell (2004) 16:1419-1432.
Sukumvanich et al., Cell Motil. Cytoskel. (2004) 59:141-152.
Tse et al., Plant Physiol. (2006) 142:1442-1459.
Verslues et al., Plant Journal (2006) 47:776-787.

* cited by examiner

*Primary Examiner* — Cathy Kingdon Worley
(74) *Attorney, Agent, or Firm* — Morrison & Foerster LLP (57) ABSTRACT

Methods to alleviate abiotic stress by modifying plants or plant cells to contain a heterologous nucleic acid that comprises a nucleotide sequence encoding the purple acid phosphatase activity of soybean GmPAP3 fused to a mitochondrion-targeting transit peptide are disclosed. Such abiotic stress can include enhanced salinity, dehydration and oxidative stress.

6 Claims, 11 Drawing Sheets

Figure 1

Confocal microscopic studies of the subcellular localization of GmPAP3

Figure 2A

Western blot analysis of GmPAP3 using mitochondria-enriched protein fraction

Figure 2B

Electron microscopic studies of GmPAP3

Figure 3

Mitochondrial membrane integrity under salinity and osmotic stresses

Figure 4

Cell viability under salinity and osmotic stresses.

Lipid peroxidation in plants under oxidative stress

METHOD TO ALLEVIATE ABIOTIC STRESS IN PLANTS BY EXPRESSION OF MITOCHONDRIAL-TARGETED PURPLE ACID PHOSPHATASE

RELATED APPLICATION

This application claims benefit of U.S. application Ser. No. 60/838,769 filed 18 Aug. 2006. The contents of this document are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 549072000200Seqlist.txt | Aug. 28, 2008 | 655 bytes |

TECHNICAL FIELD

The invention is in the field of plant genetic engineering. More specifically, it concerns the use of a purple acid phosphatase (PAP) protein targeted to the mitochondrion to alleviate stresses caused by salinity and drought and by oxidative stress.

BACKGROUND ART

Plants may be subjected to a wide variety of stress conditions that are induced by non-living agents or circumstances such as drought, enhanced salinity, temperature stress, and the like. Deviations from the norm in either direction will constitute an abiotic stress. It is understood that hyper salinity and drought lead to oxidative stress through the accumulation of reactive oxygen species (ROS) and metabolic changes in the plant will generally arise as a result of these stress conditions. A general discussion of genes that are regulated in response to stress is set forth in U.S. Patent Publications 2002/0160378 and 2004/0009476, which appear to be based on the same application.

The present inventors, in an article appearing in 2003 (Liao, H, et al., *GENE* (2003) 318:103-111) cloned and sequenced a novel purple acid phosphatase-like gene in soybean, designated GmPAP3 that was induced by enhanced salinity, but not by phosphorus deficiency as were many PAP genes. The authors further noted that the nucleotide sequence encoding this protein included a putative mitochondrion targeting transit peptide (MTTP) and speculated that the protein would reside mainly in the mitochondrion.

It has now been confirmed that the expressed GmPAP3-encoded protein is located in mitochondria and can confer tolerance of plants or plant cells with respect to abiotic stress conditions.

DISCLOSURE OF THE INVENTION

Applicants have demonstrated that the purple acid phosphatase of soybean is mainly present in the mitochondria of plant cells and is able to counteract the accumulation of reactive oxygen species (ROS). Thus, mitochondrial-directed PAP protein is able to counteract abiotic stress by increasing the percentage of cells that retain intact mitochondria, reducing the percentage of dead cells, and reducing the accumulation of ROS. This has the effect as well of inducing better root growth and less lipid peroxidation in response to herbicide application.

Accordingly, in one aspect, the invention is directed to a method to protect plant or plant cells from abiotic stress which method comprises modifying said plant or plant cell to produce a purple acid phosphatase targeted to the mitochondria.

In other aspects, the invention is directed to recombinant expression systems useful for modifying plants or plant cells to conduct the method of the invention.

BRIEF DESCRIPTION OF THE DRAWINGS

FIGS. 2A-2B show immunodetection of GmPAP3.

MODES OF CARRYING OUT THE INVENTION

It has been found that purple acid phosphatase (PAP) activity targeted to the mitochondrion is successful in conferring tolerance in plant cells and plants with respect to abiotic stress factors and in particular hypersalinity, dehydration, and oxidative stress, which oxidative stress may be exhibited by accumulation of reactive oxygen species (ROS) and may be a secondary response to primary stress factors. Plants and plant cells can exhibit this tolerance by virtue of transgenic modification to include expression systems which result in the production of proteins that target PAP activity to the mitochondria. This is illustrated below in tobacco plant cells and in *Arabidopsis* plants, but is by no means limited to these examples. Any higher plant or cell of a higher plant is a suitable subject for the methods and materials of the present invention.

In order to provide the requisite targeted PAP protein, plant cells are modified to contain nucleotide sequences encoding the relevant protein, optionally operably linked to control sequences operable in plants, or integrated into the genome so as to be expressed under the control of endogenous control sequences. Nucleic acid constructs may contain control sequences operable in plants operably linked to the MTTP-PAP encoding sequence, which control sequences can be selected to result in constitutive, tissue-specific or non tissue-specific, or inducible expression. A wide variety of such control sequences is available in the art, and appropriate vectors for genetic modification are also well known and, indeed, commercially available. Similarly, techniques for effecting genetic modification of plant cells and reconstituting intact plants are now well known in the art. A useful summary of the state of the art in this respect, including a reasonably comprehensive list of the types of plants and plant cells that can form the subjects of the present invention is found in U.S. Patent Publication 2004/0009476, published 14 Jan. 2004, noted above, and incorporated herein by reference with respect to its disclosure of appropriate techniques for genetic manipulation of plants and the range of plants and plant cells to which these techniques may be applied.

Further, because the modified cells and plants of the invention are resistant to stress caused by osmotic, high salinity and/or oxidative stress, an expression system comprising a nucleotide sequence encoding the MTTP-PAP fusion operably linked to control sequences operable in plants can be used as a selectable marker for successful transformation of cells. Successful transformants are more highly resistant and survive an applied stress for which the marker confers tolerance. Hence, successful transformants can be identified by virtue of their ability to survive such stress conditions.

The MTTP-PAP fusion proteins of the invention comprise an amino acid sequence that confers PAP activity and a sequence that effects the transit of the fused protein to the mitochondria, positioned in such a way that the MTTP is operable to transport the fusion protein. One such fusion protein is found natively, as described above, in soybeans and was designated GmPAP3 by Liao, H., et al. (supra). However, nucleotide sequences that encode proteins with PAP activity from other sources or indeed other PAP encoding sequences from soybeans can also be used in the invention by preparing a construct which includes the MTTP-encoding sequence in operable linkage thereto. Accordingly, the invention includes such constructs.

The ability of the MTTP-PAP fusion to confer tolerance to hypersalinity, osmotic and/or oxidative stress such as conferred by the herbicide Paraquat, can be exhibited in numerous ways, including amelioration of ROS, retention of intact mitochondria, maintenance of viability, enhanced growth of various plant parts, and general improvement in cellular health.

The following examples and results confirm and illustrate the success of the methods and constructs of the invention.

The following protocols resulted in the data set forth in Examples 1-6 below.

Establishment of Transgenic Tobacco BY-2 Cell Lines and Transgenic *Arabidopsis thaliana*

Recombinant constructs containing GmPAP3 or GmPAP3-T7 under the control of the constitutive Cauliflower Mosaic Virus 35S promoter were cloned into a binary vector (Brears, et al., *Plant Physiol*. (1993) 103:1285-1290) and introduced into *Agrobacterium*. The constructs were transformed into BY-2 cells (GmPAP3 and GmPAP3-T7) or *A. thaliana* (GmPAP3) respectively using a co-cultivation method (An, G., *Plant Physiol*. (1985) 79:568-570) or a vacuum infiltration protocol (Bechtold and Pelletier, J. Martinez-Zapater, J. Salinas, eds, *Arabidopsis Protocols*. Humana Press Inc., Totowa (1993) pp 259-266). After selecting the transformants on antibiotic-containing media, PCR screening using gene specific primers was performed to verify the successful integration of the transgene into the genomes; and Northern blot analysis was performed to confirm the expression of the transgenes in the transgenic cell and plant lines. For transgenic *A. thaliana*, seeds of T3 homozygous lines with single insert were obtained and used in subsequent physiological studies.

Gene Expression Study

To study the gene expression patterns of GmPAP3 under NaCl and PEG treatment, surface-sterilized soybean (*Glycine max* L. Merr. cv. Union) seeds were first germinated in filter papers containing modified Hoagland's solution (4.5 mM $KNO_3$, 3.6 mM $Ca(NO_3)_2$, 1.2 mM $NH_4NO_3$, 3.0 mM $MgSO_4$, 1.2 mM $(NH)_2SO_4$, 0.25 mM $KH_2PO_4$, 4.5 µM $MnSO_4$, 4.5 µM $ZnSO_4$, 1.5 µM $CuSO_4$, 0.4 µM $(NH_4)_6Mo_7O_{24}$, 0.09 mM Fe-EDTA, and 1.5 µM $H_3BO_3$). After germination, one-week-old seedlings of uniform growth stage were transferred to a hydroponic system containing the same culture medium. After opening of the first trifoliate, seedlings were treated with modified Hoagland's solution supplemented with 125 mM NaCl and 5% PEG, respectively. The youngest fully expanded trifoliate of treated plants were collected for total RNA extraction after 48 h. To study the gene expression pattern of GmPAP3 under paraquat (PQ) treatment, surface sterilized seeds were germinated in silicon sand containing half Hoagland's solution. After germination, 10-day-old seedlings of uniform growth stage were transferred to a hydroponic system containing the same culture medium. After equilibration of the seedlings for 24 d, 10 mM PQ solution was sprayed on both surfaces of trifoliate leaves and leaf samples were collected after 4 h.

Northern blot analysis was performed using antisense single-stranded DNA probes labeled with digoxigenin (DIG) (Roche, Mannheim, Germany) as a probe. Since GmPAP3 was cloned into the pBluescript II KS (+) vector, the T3 (5'-AATTAACCCTCACTAAAGGG-3') (SEQ ID NO:1) and T7 (5'-GTAATACGACTCACTATAGGGC-3') (SEQ ID NO:2) promoter primers were used for synthesizing the PCR probes.

Analysis of Mitochondria Integrity

Cells were treated with 200 mM NaCl for 1 h or 2% PEG for 1 h before staining with 10 µg/ml rhodamine-123 (Rh123) (R302, Molecular Probes) for 1 h. The signal of Rh123 was excited by green HeNe laser at 543 nm. The filter set HQ590/70 was used and confocal images were collected by the Bio-Rad Radiance 2100 system. 10-25 cells were counted for each sample for statistical analysis.

Cell Viability Assay

Cells were treated with 200 mM NaCl for or 2% PEG for 24 h before staining with 0.4% trypan blue (T8154, Sigma). Stained cells were observed under light microscope. Around 200 cells were counted for each sample.

Detection of ROS

The chemical probe $H_2DCFDA$ has been used extensively as a non-invasive, in vivo measure of intracellular ROS (Allan, et al., *Plant Cell* (1997) 9:1559-1572); Maxwell, D. P., et al., *Proc. Natl. Acad. Sci. USA* (1999) 96:8271-8276). Cells were pre-stained with dichlorodihydrofluorescein diacetate ($H_2DCFDA$) for 30 min before treatment with 200 mM NaCl for 1 h or 2% PEG for 1 h. The signals of $H_2DCFDA$ were excited by 488 nm Argon laser and the HQ 515/30 filter set was used. The same level of laser excitation, iris and gain were used for each cell analyzed. The fluorescence intensity of $H_2$DCFDA was estimated by using the program described in the National Institutes of Health website on the World Wide Web located at rsb.info.nih.gov/ij/. Quantitative analysis was done by tracing the entire cell (by using the selection tools) and the total fluorescence intensity was measured. This fluorescence intensity measurement (in pixels) was then divided by the area of the cell to obtain average pixel fluorescence intensity. In addition, background fluorescence intensity was measured in the same field and was subtracted. 10-20 cells were analyzed for each sample to perform statistical analysis.

Subcellular Localization of GmPAP3

The subcellular localization of GmPAP3 was studied by using a GmPAP3-T7 fusion protein. The location of the T7 tag was visualized by immunolabeling with FITC-conjugated secondary antibody. BY-2 cell fixation and confocal immunofluorescence were carried out according to (Jiang and Rogers, *J. Cell Biol.* (1998) 143:1183-1199) with minor modifications. Cells were prestained with the mitochondria marker MitoTracker Orange™ (M7510, Molecular Probes) before the fixation and immunolabeling process. The signal of MitoTracker Orange™ was excited by 543 nm Green HeNe laser and the HQ 590/70 filter set was used. The signal of FITC was excited by 488 nm Argon laser and the HQ 515/30 filer set was used. All confocal images were collected by Bio-Rad Radiance 2100 system.

For quantification of the colocalization of FITC and MitoTracker Orange™ signals, superimposition of green (FITC) and magenta (MitoTracker Orange™) images resulted in yellow where the green and magenta signals overlapped. By using the program ImageJ1.34n (Sukumvanich, et al., *Cell Motil. Cytoskel.* (2004) 59:141-152), the pixel area occupied by yellow divided by the pixel area occupied by green was calculated. Images from at least 10 different cells from the double-labeling experiment were analyzed to calculate the colocalization of FITC and MitoTracker Orange™ signals.

Extraction of Mitochondrial Protein

Mitochondrial protein was extracted by means of differential centrifugation as described in Douce, R., et al., *Methods Enzymol.* (1987) 148:403-415 with modifications. Plant material was gently homogenized in 2 volumes of ice-cold extraction medium (0.25 M Sucrose, 5 mM EDTA, 1 mM EGTA, 1 mM dithioerythritol, 0.1% BSA, 0.6% PVPP in 10 mM HEPES-TRIS pH 7.4). The homogenate was filtered and squeezed through Miracloth™ and the mitochondria were immediately separated from the cytoplasmic fraction by centrifugation at 10,000 g, 10 min. The resulting crude mitochondrial pellet was resuspended in medium I (0.25 M Sucrose, 5 mM EDTA, 1 mM EGTA, 0.1% BSA in 10 mM HEPES-TRIS pH 7.4) and centrifuged at 600 g, 5 min to remove nuclei and heavy cell debris. This washing procedure was repeated two times. Washed mitochondria were resuspended in medium II (Sucrose 0.25 M, EGTA 30 µM in HEPES-TRIS 10 mM pH 7.4) and stored on ice.

Root Growth Assay of Transgenic *Arabidopsis* Under Salt Treatment

Seeds of transgenic lines (GmPAP3 and the empty vector) and their untransformed parent Columbia-0 (Col-0) were sown on vertical MS plates containing 3% sucrose and 0.9% (w/v) agar. Seedlings (7 d after germination) were transferred onto either the control MS agar plates or MS agar plates supplemented with 150 mM NaCl. The root length of each individual seedlings before and 7 d after treatment was recorded and percentage root growth was calculated.

Root Growth Assay of Transgenic *Arabidopsis* Under PEG Treatment

Seeds of transgenic lines (GmPAP3 and the empty vector) and their untransformed parent Columbia-0 (Col-0) were sown on MS plates containing 3% sucrose and 0.9% (w/v) agar. Seedlings (7 d after germination) were transferred onto either the control MS agar plates or MS agar plates supplemented with 15% Polyethylene-glycol 6000 (PEG). The root length of each individual seedlings before and 7 d after treatment was recorded and percentage root growth was calculated.

Since PEG cannot be dissolved in the agar before pouring plates (PEG will prevent agar from polymerizing), PEG treatment was brought about by using PEG-infused agar plates. The PEG-infused agar plates were prepared as described by Verslues, P. E., et al., *The Plant Journal* (2006) 47:776-787 with slight modifications. Appropriate amounts of MS were prepared for both MS agar media and PEG overlay for the number of plates needed and adjusted to pH 5.7. To the solution used to prepare the agar plates, 9 g per liter agar was added. To the solution used for the PEG overlay, no agar is added, but instead is autoclaved directly. After autoclaving, 20 ml of MS media were poured into 100 mm square plates. For the MS medium (without agar), 15% PEG was added. After the MS agar plates solidified, 30 ml of PEG overlay was added on each plate. The plates were infused in PEG overlay and allowed to equilibrate for at least 16 hr. The PEG overlay was poured off just before use and the PEG-infused plates were used immediately.

Root Growth Assay of Transgenic *Arabidopsis* Under Paraquat Treatment

Seeds of transgenic lines (GmPAP3 and the empty vector) and their untransformed parent Col-0 were sown on vertical MS plates containing 3% sucrose and 0.9% (w/v) agar. Seedlings (5 d after germination) were transferred onto either the control MS agar plates or MS agar plates supplemented with 10 µM PQ. The root length of each individual seedlings before and 7 d after treatment was recorded and percentage root growth was calculated.

Lipid Peroxides Detection

FOX assay was used to determine lipid peroxides as described (Sattler, et al., *Plant Cell* (2004) 16:1419-1432). Twelve seedlings were extracted with 400 µL of methanol: dichloromethane (1:1 [v/v]) containing 0.05% butylated hydroxytoluene and 50 µL of 150 mM acetic acid. Lipids were partitioned into the organic phase by adding 300 µL of water, vortexing and centrifugation at 3,750 g. The lipid extracts were incubated at room temperature with FOX solution (23280, Pierce) for 30 min. Immediately after incubation, the absorbance was measured at 595 nm by a microplate reader. A standard curve was constructed using hydrogen peroxide as suggested in the manufacturer's protocol. The reactivity of 18:2-derived lipid hydroperoxides (LOOHs) with the FOX reagent is nearly identical to hydrogen peroxide (DeLong, et al., *J. Agric. Food. Chem.* (2002) 50:248-254).

Statistical Analysis

Data were analyzed using the SPSS (ver. 12.0) statistical package. Samples exhibiting significant differences ($p<0.01$) were indicated.

Example 1

Location of GmPAP3 in Mitochondria

The nucleotide sequence encoding soybean GmPAP3 described in Liao, H., et al. (GENE (2003) 318:103-111, supra.) was cloned into an expression vector compatible with tobacco cells as a fusion protein with T7 as described above. This expression vector was used to transform tobacco BY-2 cells.

Subcellular localization of GmPAP3 was studied by confocal immunofluorescence localization. FITC-conjugated secondary antibody was used to label the GmPAP3-T7 tag fusion protein produced in BY-2 cells. MitoTracker Orange™ fluorescence dye was used to specifically label mitochondria. Percent of colocalization for the signal of FITC and MitoTracker Orange™ was expressed as amount of FITC colocalized with MitoTracker Orange™ signal. Percent colocalization is expressed as the mean±standard deviation (SD) for the number of cells analyzed, as shown below.

| GmPAP3-T7 transgenic cell lines | Percentage colocalization (mean ± SD) | No. of cells analyzed |
|---|---|---|
| 1535-1 | 66.11 ± 5.56% | 29 |
| 1535-2 | 64.84 ± 4.16% | 31 |
| 1535-3 | 67.20 ± 4.69% | 27 |
| 1535-4 | 62.33 ± 3.33% | 17 |

Figure 1:
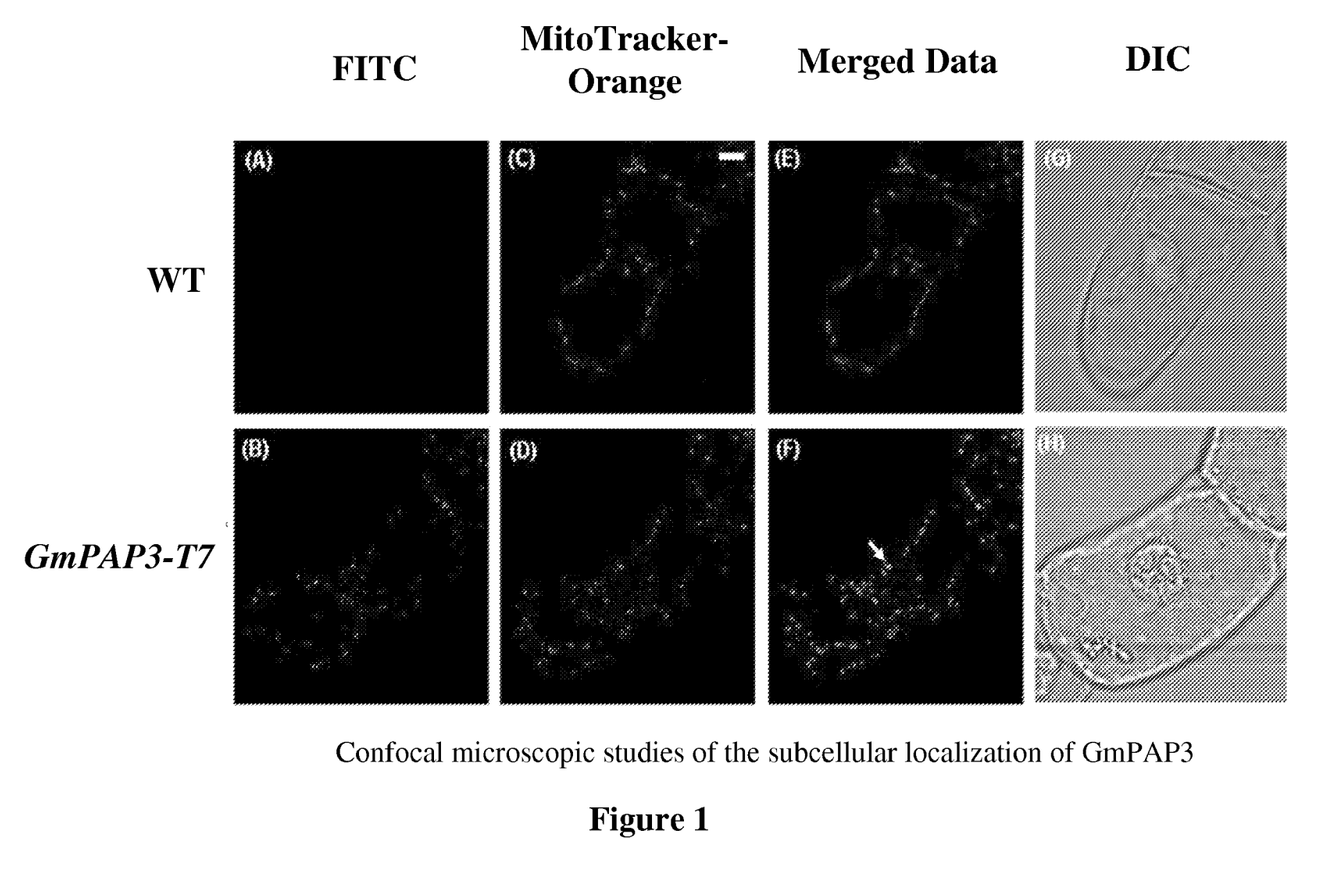
FIG. 1 shows a comparison of wild type tobacco BY-2 cells and transgenic tobacco BY-2 cells that have been modified to contain an expression vector for GmPAP3-T7 fusion protein.

The results for wild type and 1535-2 are also shown in FIG. 1.

Example 2

Alternative Measure of Colocalization of GmPAP3 in Mitochondria

Figure 2A:
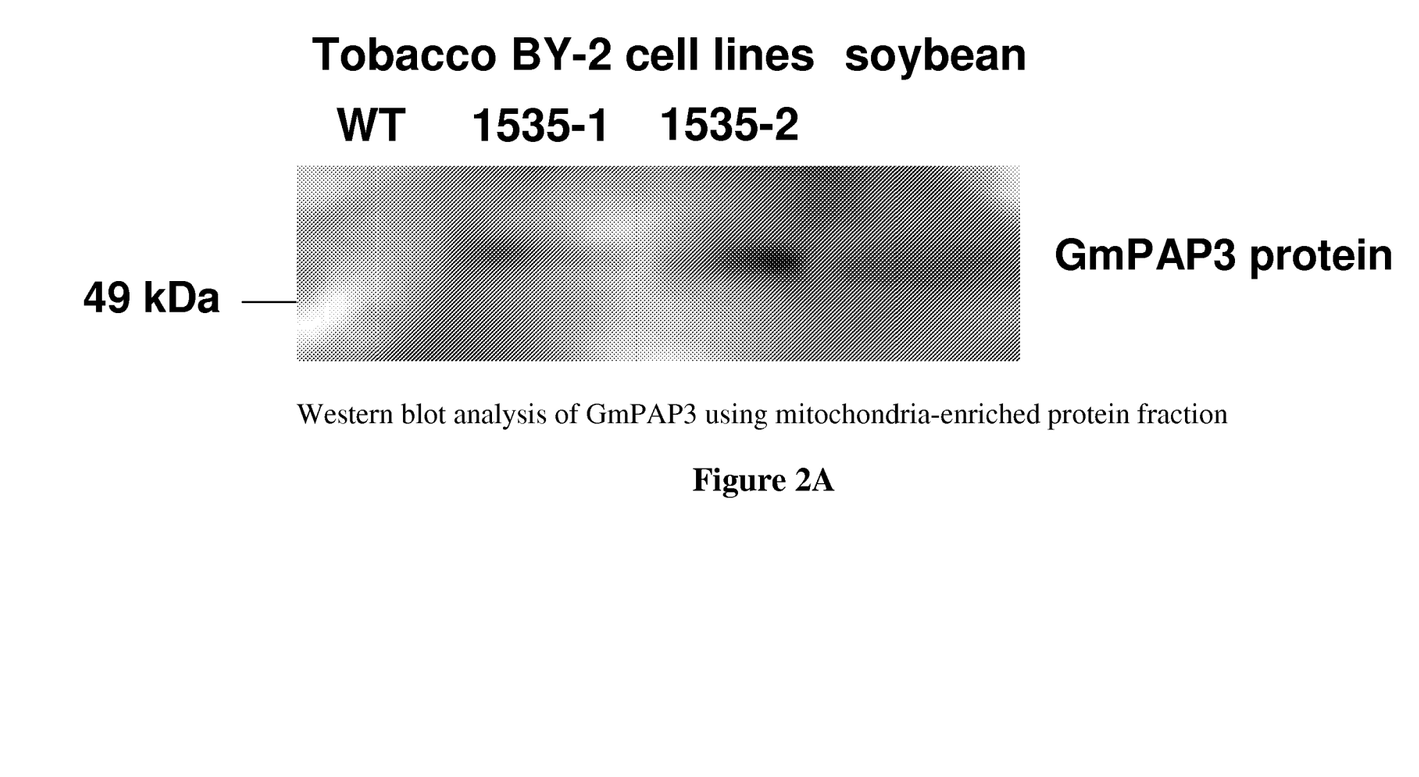
FIG. 2A shows a Western blot indicating the presence of soybean GmPAP3 protein in mitochondria-enriched protein fractions from BY-2 cell lines.

The transgenic BY-2 cells provided in Example 1 were cultured to effect production of GmPAP3. Mitochondrial protein was extracted and GmPAP3 specific antibody was used for immunodetection. The results are shown in FIG. 2A, where WT indicates mitochondrial protein fraction from wild type BY-2 cell lines; 9111 and 9112 show mitochondrial protein extracted from GmPAP3 transgenic cell lines; J23 shows mitochondrial protein extracted from the soybean cultivar J23. As seen GmPAP3 migrates to the mitochondrial fraction.

Figure 2B:
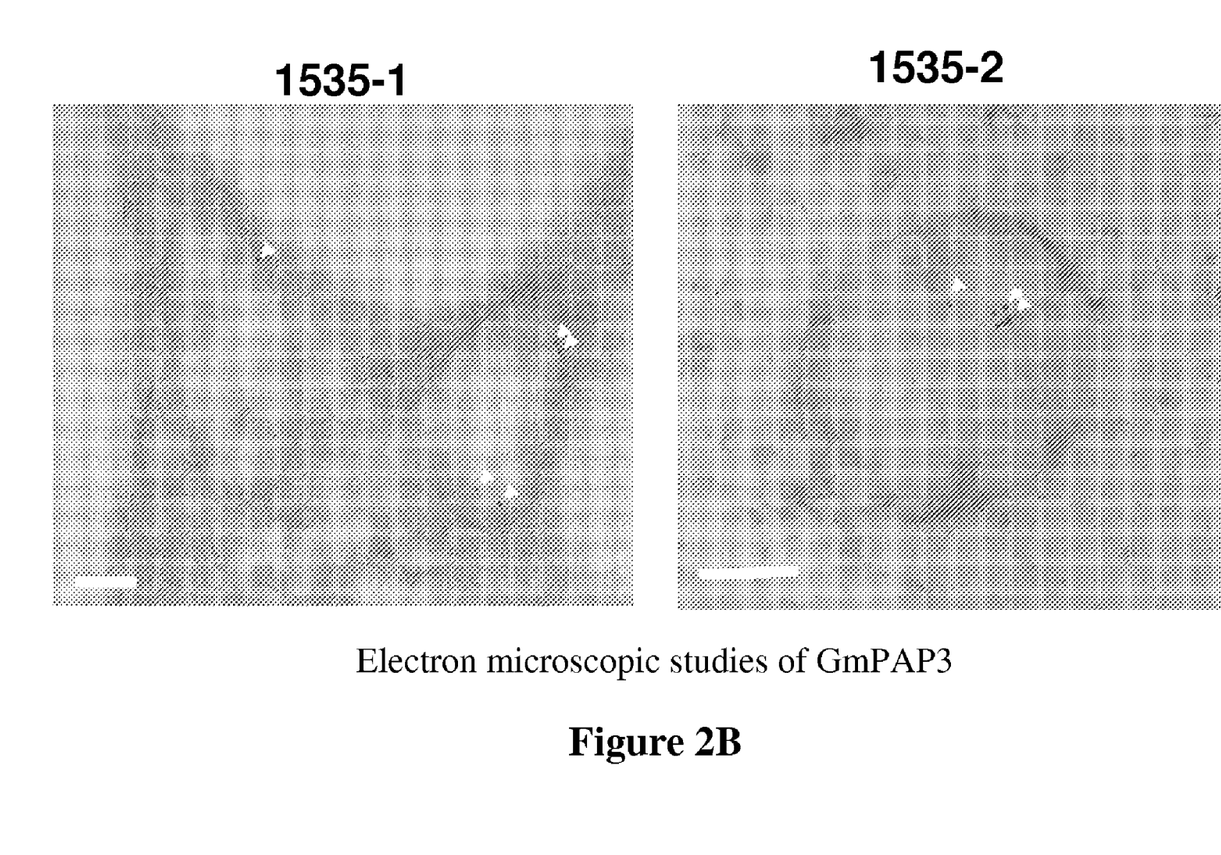
FIG. 2B shows electron microscope detection using the GmPAP3 antibody employed in FIG. 2A in two independent GmPAP3-T7 transgenic cell lines (1535-1, 1535-2). Arrowheads indicate the location of gold particles that were mostly found in mitochondria. Scale bar=200 nm.
Figure 3:
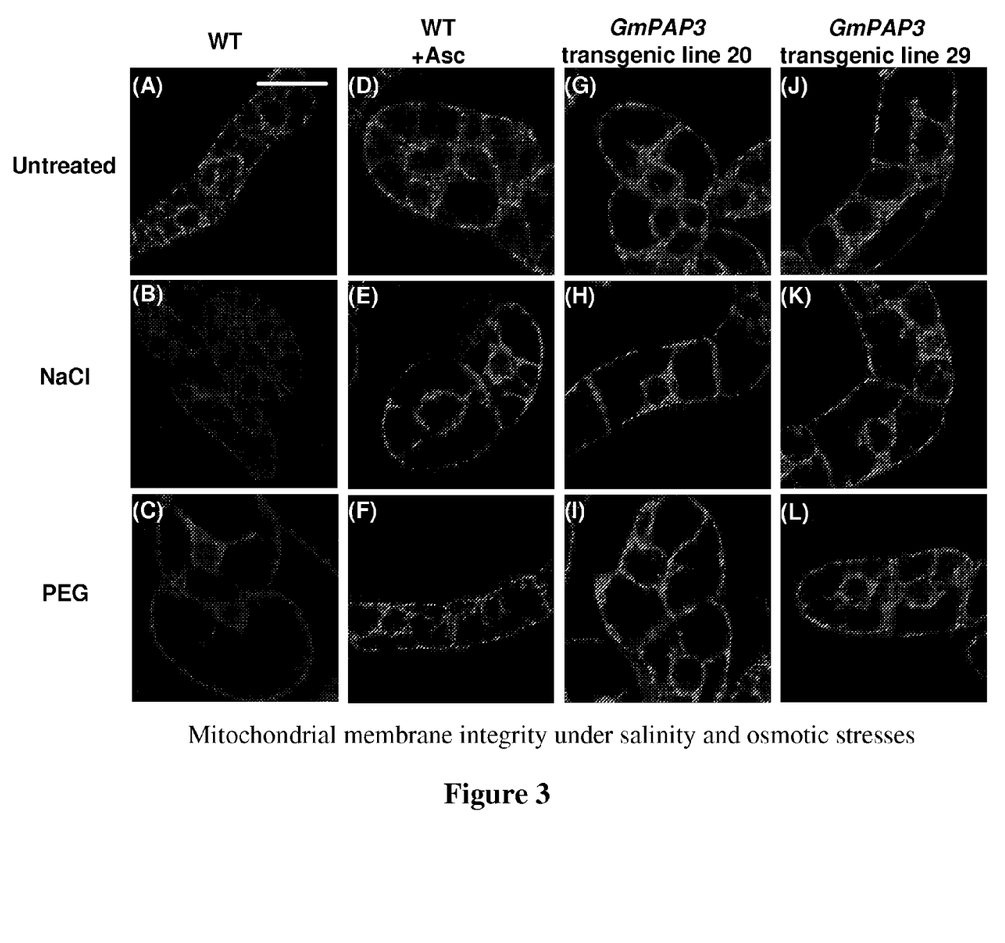
FIGS. 3A-3L show the effect of GmPAP3 on the ability of transgenic BY-2 cells to survive salinity and osmotic stress.
Figure 4:
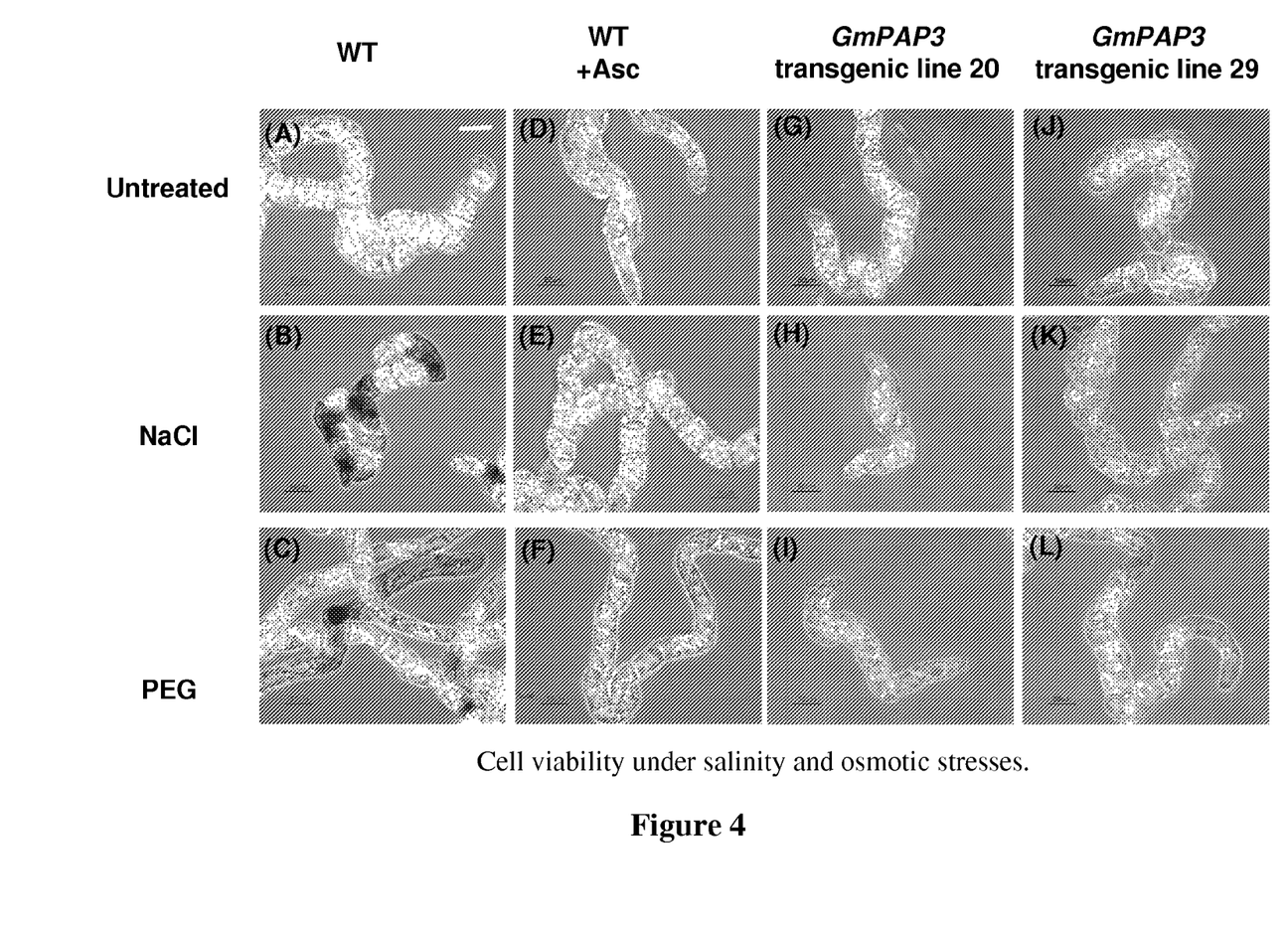
FIGS. 4A-4L show the effect of GmPAP3 on the ability of BY-2 cell lines to remain viable in the presence of salinity or osmotic stress.
Figure 5:
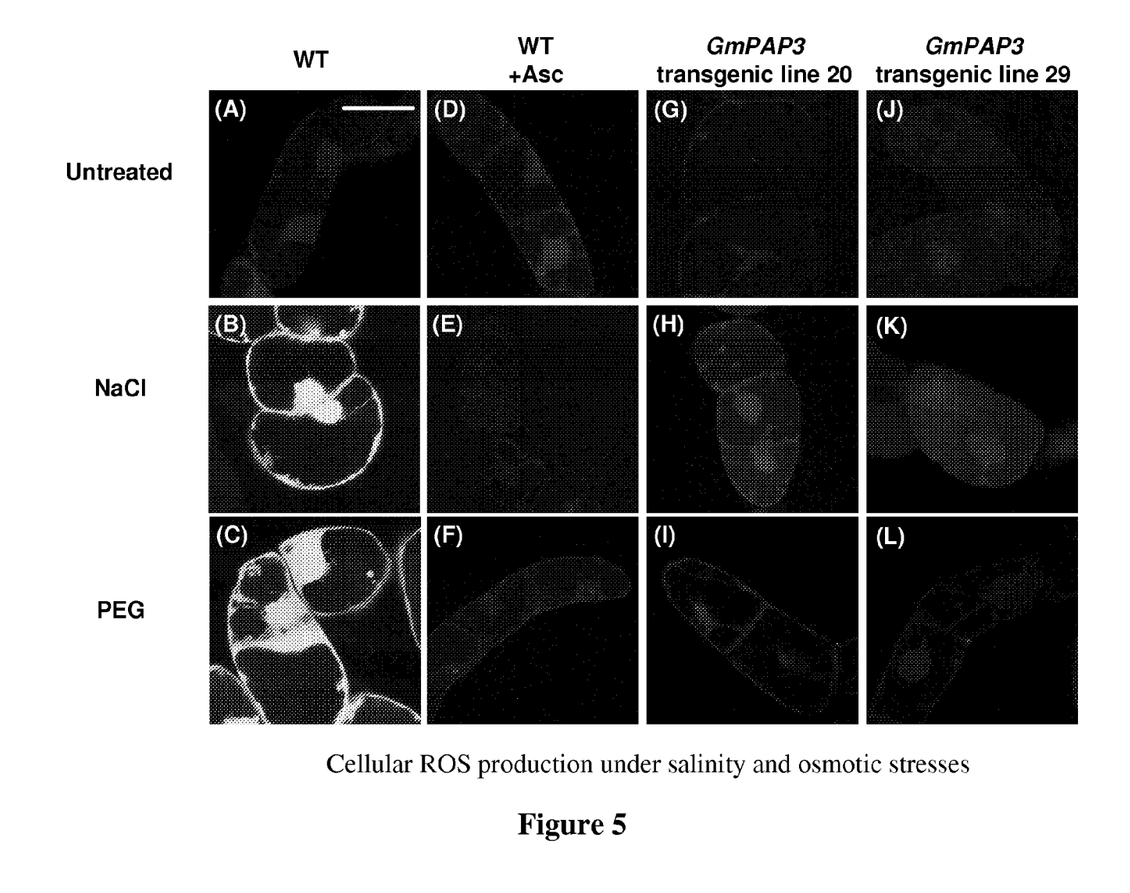
FIGS. 5A-5L are pictorial representations of the effect of expression of mitochondrion-targeted GmPAP3 on the ROS accumulation in BY-2 cells.

FIG. 2B shows an alternative demonstration of the results in FIG. 2A. Embedding and electron microscopy were performed as described by Tse, Y. C., et al., *Plant Physiol.* (2006) 142:1442-1459) with slight modifications. Samples were fixed in a primary fixative solution contain 0.25% (v/v) glutaraldehyde and 1.5% (v/w) paraformaldehyde in 50 mM phosphate buffer, pH 7.4, for 15 min at room temperature before incubating at 4° C. for an additional 16 h. After washing with phosphate buffer at room temperature, cells were dehydrated in an ethanol series and then embedded in Lowicryl® (HM20) resin. Ultrathin sections were than prepared from these blocks using Ultracut S (Leica, Wetzlar, Germany). The GmPAP3-specific antibody was used as the primary antibody followed by detection using the gold-conjugated anti-rabbit secondary antibody. Immuno-labeled sections were then post-stained with 4% uranyl acetate and examined using a transmission electron microscope (JEM-1200EXII, JEOL, Tokyo, Japan).

Example 3

Effect of GmPAP3 on Mitochondrial Membrane Integrity Under Salinity and Drought Stresses Transgenic BY-2 cell lines prepared as in Example 1 were cultured to express the GmPAP3 protein and subjected to treatment with sodium chloride or polyethylene glycol (PEG, osmotic stress) as explained above and in the description of the results as shown in FIGS. 3A-3L. The results on mitochondrial integrity were compared with the effect of the presence of ascorbic acid. The results are shown in the table below which summarizes the data in FIGS. 3A-3L. The data are the results of counting 10-25 cells and the experiment repeated 3 times. The percentage was presented as the mean value of 3 experiments±SD, where ** denotes statistical difference ($p<0.01$) from the wild type BY-2 cells under the same treatment, based on one-way ANOVA followed by the Turkey test.

| | % cells with intact mitochondria | | |
|---|---|---|---|
| Cell lines | Control | NaCl | PEG |
| Wild type BY-2 | 100% | 45.27 ± 6.3 | 47.98 ± 3.1 |
| Wild type BY-2 + 10 mM ascorbic acid | 100% | 86.20 ± 3.3** | 82.16 ± 3.7** |
| GmPAP3 transgenic cell line 20 | 100% | 81.36 ± 3.9** | 81.32 ± 5.6** |
| GmPAP3 transgenic cell line 29 | 100% | 80.40 ± 4.7** | 79.5 ± 6.9** |

Wild type (WT) BY-2 cells (FIGS. 3A-3C) and GmPAP3 transgenic BY-2 cell lines #20 and #29 (FIGS. 3G-3I and FIGS. 3J-3L, respectively) without ascorbic acid supplements and wild type BY-2 cells with 10 mM ascorbic acid supplements (+Asc) (FIGS. 3D-3F) were pre-treated in a cell culture medium without stress (FIGS. 3A, 3D, 3G and 3J), with 200 mM NaCl for 1 hr (FIGS. 3B, 3E, 3H and 3K), or with 2% PEG for 1 h (FIGS. 3C, 3F, 3I, 3L) before staining with 10 μg/mL Rh123 for another hour. The signal of Rh123 was observed using a confocal laser scanning microscope (see materials and methods). 10-25 cells were counted for each line. Scale bar=50 μm.

Example 4

Effect of Stress on Viability Protection by GmPAP3

The experiment of Example 3 was performed but using viability as an assessment rather than mitochondrial integrity. Viability was evaluated by staining with trypan blue. Cells were treated with 200 mM NaCl or 2% PEG for 24 h before staining with trypan blue. The percentage was presented as the mean value of around 200 cells±SD, and shown in the table below, where ** denotes statistical difference ($p<0.01$) from the wild type BY-2 cells under the same treatment, based on one-way ANOVA followed by the Turkey test. The exponents $a$ and $b$ indicate two separate sets of experiments.

| | % of viable cells | | |
|---|---|---|---|
| Cell lines | Untreated | 200 mM NaCl | 2% PEG |
| Wild type BY-2$^a$ | 98.70 ± 2.5 | 48.30 ± 8.8 | 66.81 ± 8.2 |
| Wild type BY-2 + 10 mM ascorbic acid$^a$ | 97.52 ± 5.9 | 92.68 ± 8.0** | 94.87 ± 9.2** |
| Wild type BY-2$^b$ | 93.41 ± 10.6 | 42.14 ± 6.9 | 60.63 ± 13.2 |
| GmPAP3 transgenic cell line 20$^b$ | 94.61 ± 6.0 | 79.70 ± 16.7** | 95.96 ± 6.1** |
| GmPAP3 transgenic cell line 29$^b$ | 98.14 ± 2.6 | 85.97 ± 18.1** | 91.76 ± 12.6** |

Similar results were obtained using histological evaluation as shown in FIGS. 4A-4L. Wild type (WT) BY-2 cells (FIGS.

4A-4C) and GmPAP3 transgenic BY-2 cell lines #20 and #29 (FIGS. 4G-4I and FIGS. 4J-4L, respectively) without ascorbic acid supplements and wild type BY-2 cells with 10 mM ascorbic acid supplements (+Asc) (FIGS. 4D-4F) were pre-treated in a cell culture medium without stress (FIGS. 4A, 4D, 4G and 4J), with 200 mM NaCl (FIGS. 4B, 4E, 4H and 4K) for 24 h, or with 2% PEG (FIGS. 4C, 4F, 4I, 4L) for 24 h. Treated cells were stained with 0.4% trypan blue. Non-viable cells were stained blue. Around 200 cells were counted for each line. Scale bar=50 μm.

Example 5

Effect of GmPAP3 on ROS

GmPAP3 reduces ROS accumulation in BY-2 cells when subjected to salt and osmotic stresses, as shown in FIGS. 5A-5L. Wild type (WT) BY-2 cells (FIGS. 5A-5C) and GmPAP3 transgenic BY-2 cell lines #20 and #29 (FIGS. 5G-5I and FIGS. 5J-5L, respectively) without ascorbic acid supplements and wild type BY-2 cells with 10 mM ascorbic acid supplements (+Asc) (FIGS. 5D-5F) were pre-stained with $H_2DCFDA$ for 30 min before placed in a cell culture medium without stress (FIGS. 5A, 5D, 5G, 5J), with 200 mM NaCl for 1 h (FIGS. 5B, 5E, 5H, 5K), or with 2% PEG for 1 h (FIGS. 5C, 5F, 5I, 5L). The signals of $H_2DCFDA$ were observed using a confocal laser scanning microscope. 10-20 cells were counted for each line. Scale bar=50 μm.

Figure 6:
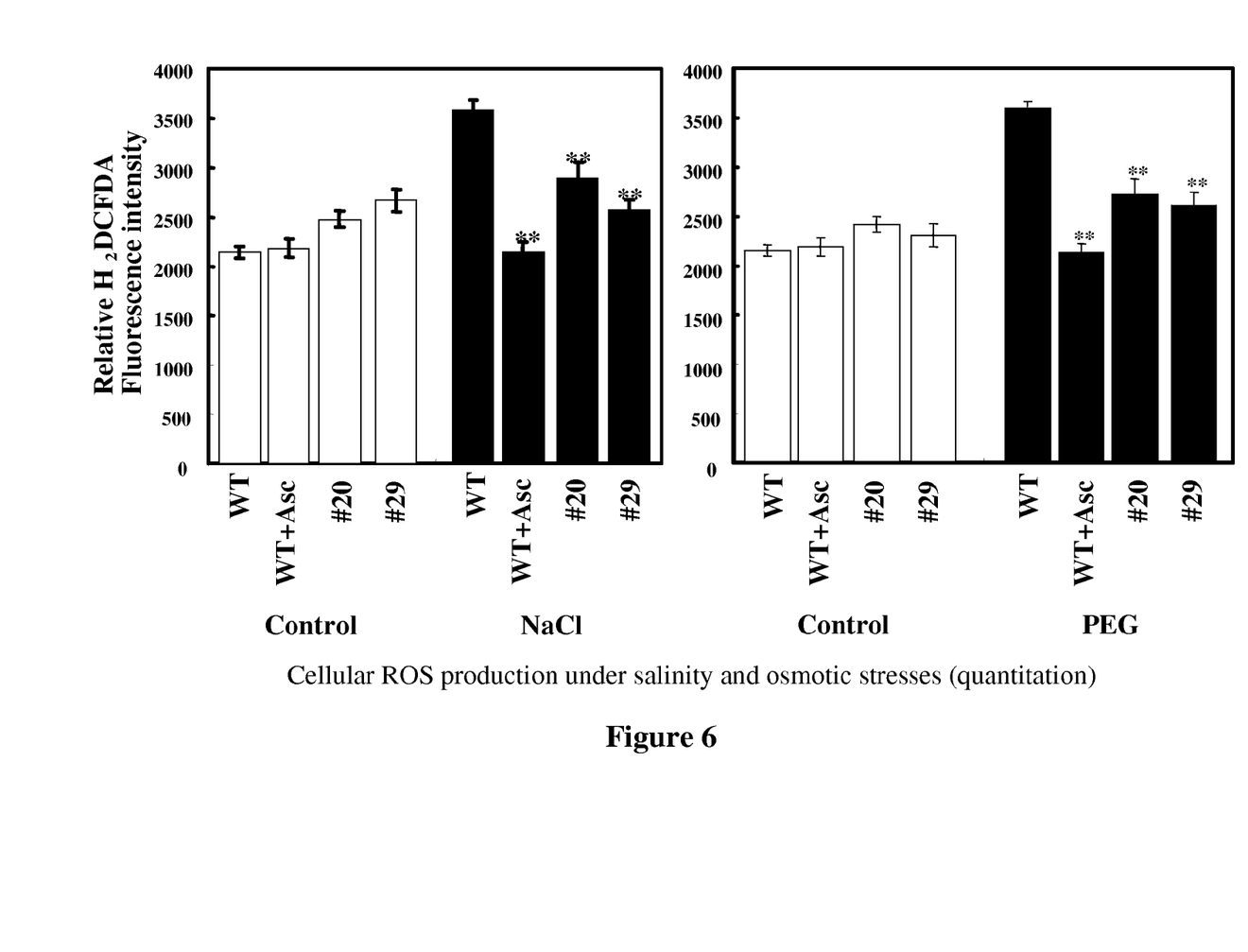
FIG. 6 is a graphical representation of the results in FIGS. 5A-5L a representation of the effect of expression of mitochondrion-targeted GmPAP3 on the ROS accumulation in BY-2 cells.

These results can also be shown graphically as shown in FIG. 6.

Fluorescence intensity was calculated by ImageJ and data obtained were analyzed by one-way analysis of variance (ANOVA) test, in which case significant differences between individual lines were determined by the Turkey's test. * indicated mean difference (compared to wild type) is significant at $p<0.05$ level and ** indicates that the mean difference is significant at $p<0.01$ level.

Example 6

Effect of GmPAP3 on Response to Stress in *Arabidopsis*

*Arabidopsis* lines F42 and C25 which have been modified to produce GmPAP3 as described above were used in these experiments. First, the effects of salt stress on root growth of *Arabidopsis* were studied. Seeds from the wild type parent (Col 0), empty vector transgenic control (V7) and two independent GmPAP3 transgenic lines (F42 and C25) were sown on MS agar plates. Young seedlings were transferred to either the control MS agar plates (CT) or MS agar plates supplemented with 150 mM NaCl. Percentage growth of root was estimated and shown in FIG. 7. Error bar: standard error. N=48. Data obtained were analyzed by one-way analysis of variance (ANOVA) test, in which case significant differences between individual lines were determined by the Turkey's test. ** indicates that the mean difference (compared to wild type) is significant at $p<0.01$ level.

Figure 7:
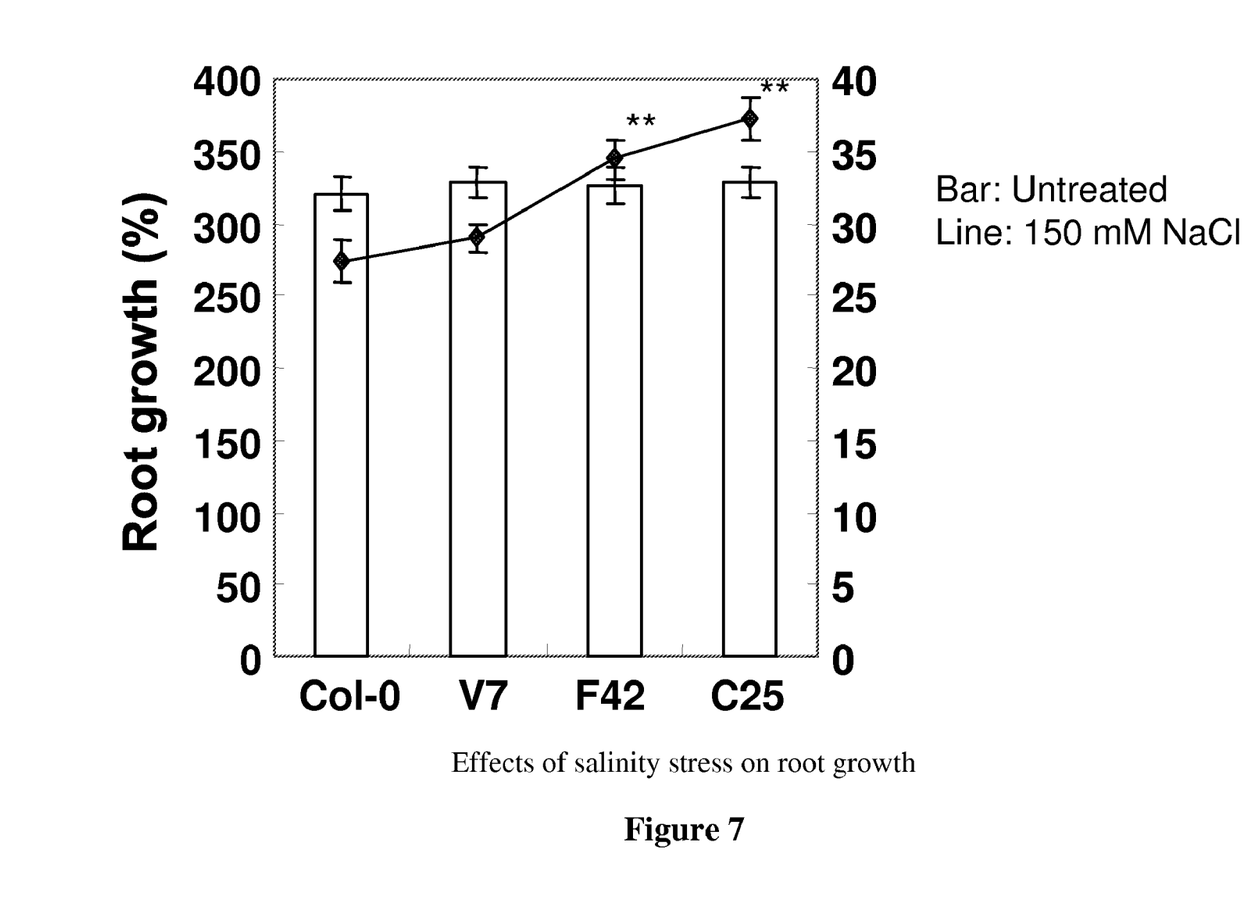
FIG. 7 shows the effect of GmPAP3 on the root growth of transgenic *Arabidopsis* under salt stress.

As shown in FIG. 7, the presence of salt actually enhanced the growth of roots in the transformance, although it diminished the growth in wild type.

Figure 8:
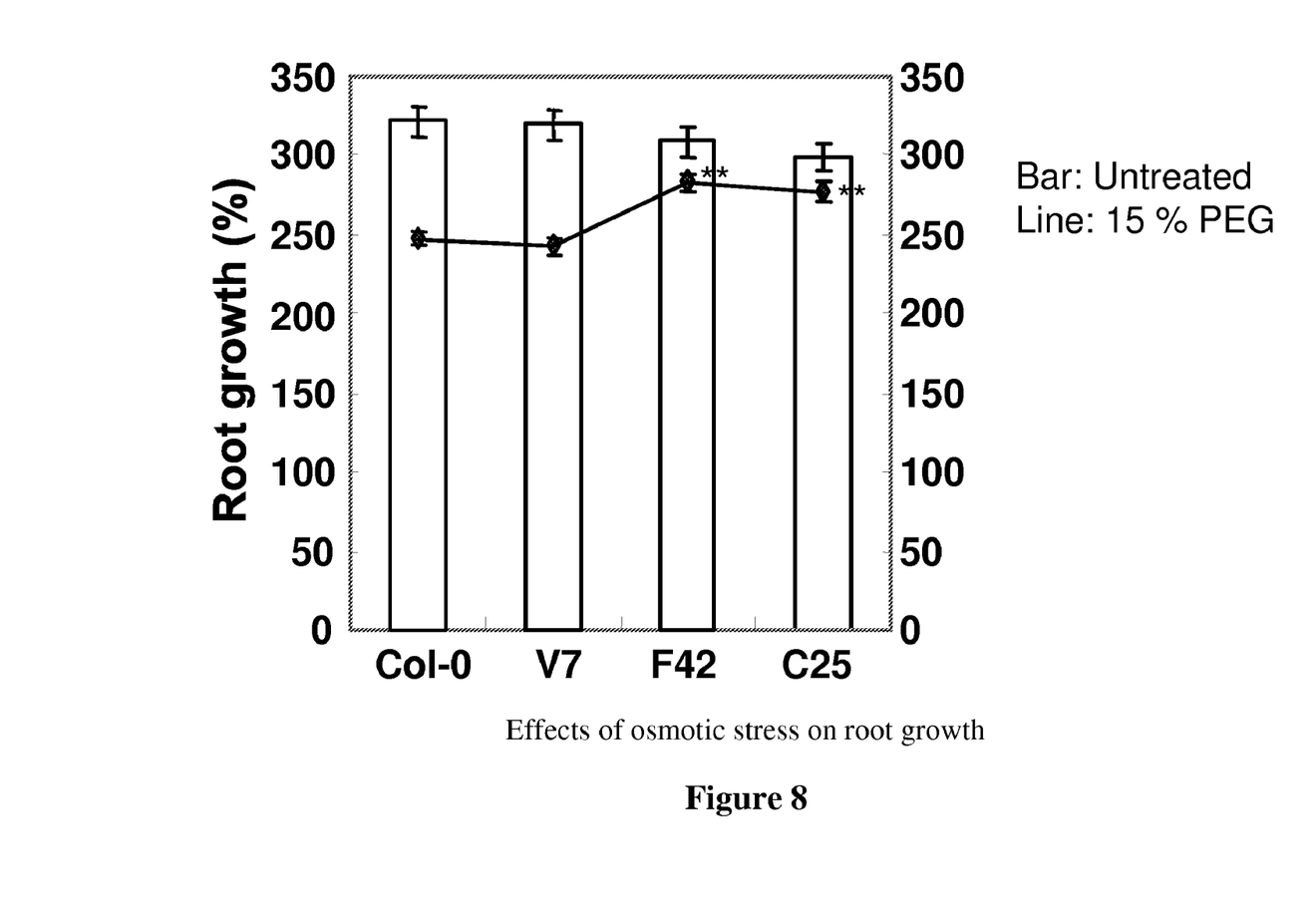
FIG. 8 shows the effect of GmPAP3 on transgenic *Arabidopsis* under osmotic stress as measured by root growth.

Next, the effects of PEG stress on root growth of *Arabidopsis* were studied. Seeds from the wild type parent (Col 0), empty vector transgenic control (V7) and two independent GmPAP3 transgenic lines (F42 and C25) were sown on MS agar plates. Young seedlings were transferred to either the control MS agar plates (CT) or MS agar plates supplemented with 15% PEG. Percentage growth of root was estimated and shown in FIG. 8. Error bar: standard error. N=48. Data obtained were analyzed by one-way analysis of variance (ANOVA) test, in which case significant differences between individual lines were determined by the Turkey's test. ** indicates that the mean difference (compared to wild type) is significant at $p<0.01$ level.

Figure 9:
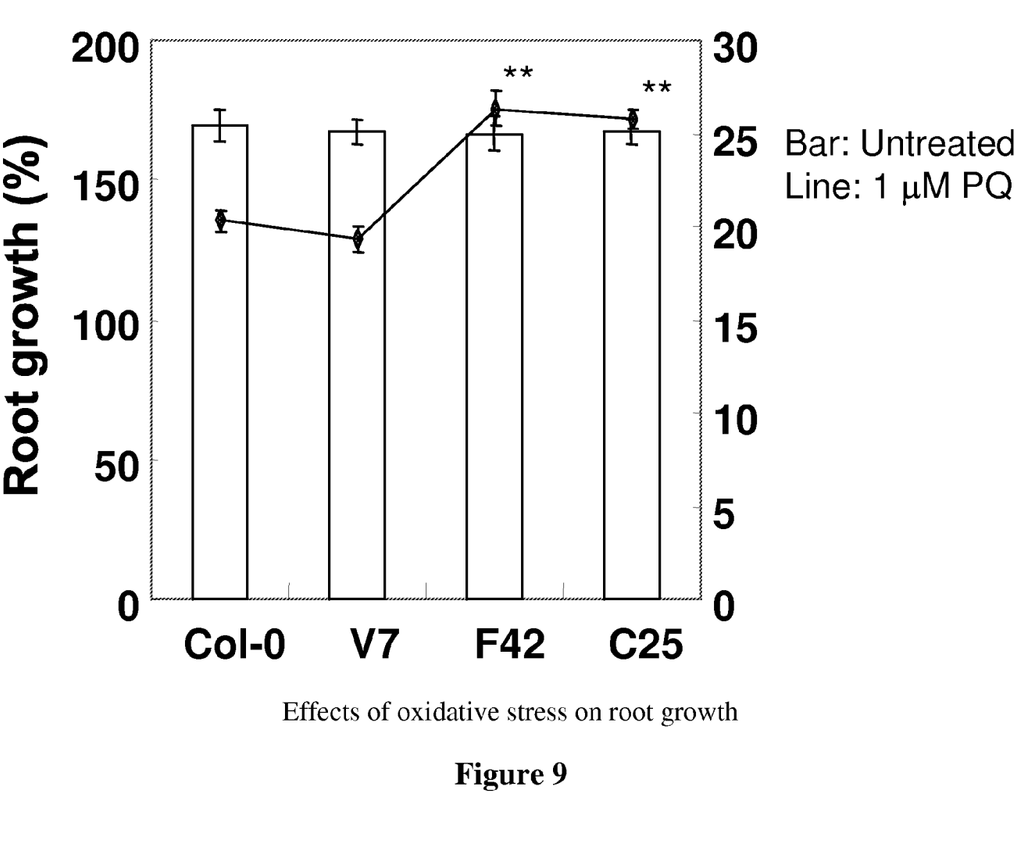
FIG. 9 shows the effect of GmPAP3 on root growth of transgenic *Arabidopsis* under oxidative stress provided by the herbicide Paraquat.

The effects of oxidative stress on root growth of *Arabidopsis* were studied. Seeds from the wild type parent (Col 0), empty vector transgenic control (V7) and two independent GmPAP3 transgenic lines (F42 and C25) were sown on MS agar plates. Young seedlings were transferred to either the control MS agar plates (CT) or MS agar plates supplemented with 1 μM Paraquat. Percentage growth of root is shown in FIG. 9. Error bar: standard error. N=48. Data obtained were analyzed by one-way analysis of variance (ANOVA) test, in which case significant differences between individual lines were determined by the Turkey's test. ** indicates that the mean difference (compared to wild type) is significant at $p<0.01$ level.

Figure 10:
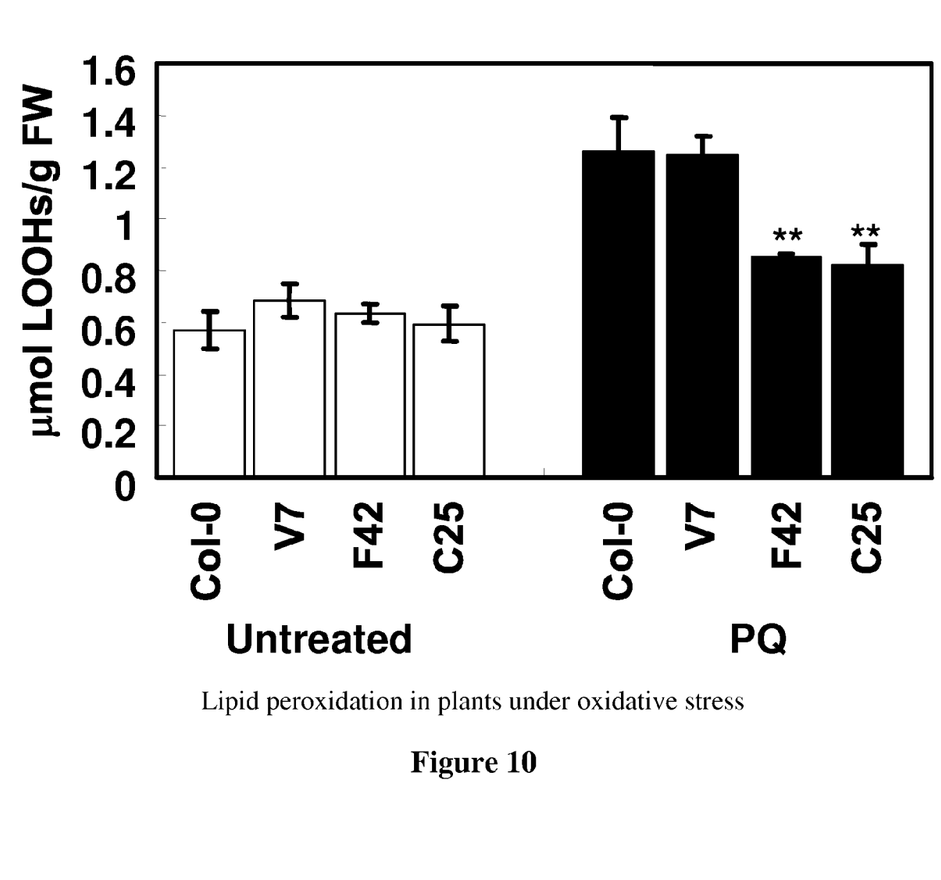
FIG. 10 is a graph showing the effect of GmPAP3 on transgenic *Arabidopsis* under oxidative treatment as measured by lipid peroxidation.

Lipid peroxidation in GmPAP3 transgenic *Arabidopsis* under oxidative treatment. Seedlings were grown and treated with Paraquat as described above. Lipid peroxidation was measured by the FOX assay and the results shown in FIG. 10. The reactivity of 18:2-derived lipid hydroperoxides (LOOHs) levels were expressed in μmole LOOHs per g fresh weight (FW). Error bar: standard error. N=4 (four sets of 12 seedlings for each data point). Data obtained were analyzed by one-way analysis of variance (ANOVA) test, in which case significant differences between individual lines were determined by the Turkey's test. ** indicates that the mean difference (compared to wild type) is significant at $p<0.01$ level. Open and close bars indicate untreated control and treated samples, respectively.

The invention claimed is:

1. A method to product a plant or plant cell from abiotic stress which method comprises modifying said plant or plant cell to contain a heterologous nucleic acid which comprises a nucleotide sequence encoding soybean GmPAP3 purple acid phosphatase (PAP) fused to a mitochondrion-targeting transit peptide (MTTP).

2. The method of claim 1 wherein the abiotic stress is one or more conditions selected from the group consisting of enhanced salinity, dehydration, and oxidative stress.

3. The method of claim 1 wherein said nucleotide sequence encodes a soybean GmPAP3, including its MTTP.

4. The method of claim 1 wherein the nucleotide sequence encoding the MTTP is heterologous to the nucleotide sequence encoding the GmPAP3.

5. The method of any of claims 1, 2, 3 and 4 wherein said protecting results in maintenance of intact mitochondria, and/or in diminishing reactive oxygen species (ROS), and/or maintaining viability.

6. The method of claim 1 wherein the plant or plant cells are tobacco or *Arabidopsis*.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
aattaaccct cactaaaggg                                        20

```
<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
gtaatacgac tcactatagg gc                                                22
```